(12) United States Patent
Suzuki et al.

(10) Patent No.: US 7,872,472 B2
(45) Date of Patent: Jan. 18, 2011

(54) EDDY CURRENT TESTING APPARATUS AND EDDY CURRENT TESTING METHOD

(75) Inventors: Yutaka Suzuki, Hitachi (JP); Masahiro Koike, Hitachi (JP); Tetsuya Matsui, Hitachi (JP); Kojirou Kodaira, Hitachinaka (JP); Katsumi Isaka, Mito (JP); Mitsuru Odakura, Hitachi (JP); Kenji Tayama, Mito (JP); Kazuhiro Suzuki, Hitachi (JP); Kenji Kumasaka, Hitachi (JP); Yuuji Adachi, Hitachi (JP)

(73) Assignees: Hitachi, Ltd., Tokyo (JP); Hitachi Engineering & Services Co., Ltd., Ibaraki (JP)

( * ) Notice: Subject to any disclaimer, the term of this patent is extended or adjusted under 35 U.S.C. 154(b) by 0 days.

(21) Appl. No.: 12/634,161

(22) Filed: Dec. 9, 2009

(65) Prior Publication Data

US 2010/0085043 A1 Apr. 8, 2010

Related U.S. Application Data

(62) Division of application No. 11/862,897, filed on Sep. 27, 2007.

(30) Foreign Application Priority Data

Sep. 29, 2006 (JP) .............................. 2006-267571

(51) Int. Cl.
*G01N 27/87* (2006.01)
*G01N 27/90* (2006.01)
*G01R 33/00* (2006.01)

(52) U.S. Cl. ........................................ 324/238; 324/262

(58) Field of Classification Search ................. 324/219, 324/220, 222, 228, 234, 238, 239, 240, 241, 324/242, 243, 262; 73/866.5
See application file for complete search history.

(56) References Cited

U.S. PATENT DOCUMENTS 3,718,855 A * 2/1973 Rogel et al. ................. 324/202

(Continued)

FOREIGN PATENT DOCUMENTS

EP 0241013 10/1987

(Continued)

OTHER PUBLICATIONS

S. Laborde, et al., "Ultrasonic Phased Array Inspection of Steam Turbine Blades With Pin Root Attachments Using a Matrix Probe", Power-Gen-Europe, Jun. 26-28, 2007.

(Continued)

*Primary Examiner*—Kenneth J Whittington
(74) *Attorney, Agent, or Firm*—Mattingly & Malur, P.C.

(57) ABSTRACT

An eddy current testing method for a turbine rotor including a disc, a plurality of turbine blades disposed along the periphery of the disc, and a plurality of pins for joining a blade fork portion formed on each of the plurality of turbine blades to a disc fork portion formed on the disc, the method including inserting a probe having an eddy current testing sensor into a hole formed through the disc fork portion and the blade fork portion by pulling out one of the plurality of pins in a state that the blade fork portion is still inserted into the disc fork portion; and performing eddy current testing for at least part of an internal surface of the hole by using the probe.

6 Claims, 6 Drawing Sheets

U.S. PATENT DOCUMENTS

| | | | |
|---|---|---|---|
| 3,753,096 A | 8/1973 | Wiers | |
| 4,134,067 A | 1/1979 | Woodbury | |
| 4,454,473 A * | 6/1984 | Rosauer | 324/262 |
| 4,644,274 A * | 2/1987 | Casarcia | 324/262 |
| 5,065,635 A | 11/1991 | Burtner et al. | |
| 5,140,264 A | 8/1992 | Metala et al. | |
| 5,278,498 A | 1/1994 | Vernon et al. | |
| 5,329,230 A | 7/1994 | Viertl et al. | |
| 5,424,639 A | 6/1995 | Meiffren et al. | |
| 5,479,834 A * | 1/1996 | Sanagawa et al. | 73/866.5 |
| 5,623,204 A | 4/1997 | Wilkerson | |
| 5,670,879 A | 9/1997 | Zombo et al. | |
| 6,608,478 B1 | 8/2003 | Dziech et al. | |

FOREIGN PATENT DOCUMENTS

| | | |
|---|---|---|
| EP | 0593357 | 4/1994 |
| EP | 0907077 | 4/1999 |
| FR | 2261526 | 9/1975 |
| GB | 2069708 | 8/1981 |
| GB | 2 262 346 A | 6/1993 |
| JP | 53-25383 | 8/1951 |
| JP | 60-093954 | 5/1985 |
| JP | 61-140962 | 9/1986 |
| JP | 62-225903 | 10/1987 |
| JP | 63-044162 | 2/1988 |
| JP | 04-250396 | 9/1992 |
| JP | 5-164745 A | 6/1993 |
| JP | 6-138095 A | 5/1994 |
| JP | 7-280774 A | 10/1995 |
| JP | 8-145954 | 6/1996 |
| JP | 10-47589 A | 2/1998 |
| JP | 2001-012208 | 1/2001 |
| JP | 2001/012208 | 1/2001 |

OTHER PUBLICATIONS

Partial European Search Report dated Dec. 20, 2007 in corresponding EP application No. 07 01 8941.0.

* cited by examiner

EDDY CURRENT TESTING APPARATUS AND EDDY CURRENT TESTING METHOD

CROSS-REFERENCES

This is a divisional of U.S. Ser. No. 11/862,897, filed Sep. 27, 2007, the content of which is hereby incorporated by reference.

CLAIM OF PRIORITY

The present application claims priority from Japanese application serial no. 2006-267571, filed on Sep. 29, 2006, the content of which is hereby incorporated by reference into this application.

BACKGROUND OF THE INVENTION

The present invention relates to an eddy current testing apparatus and an eddy current testing method, and more particularly, to an eddy current testing apparatus and an eddy current testing method preferably applicable to inspect internal surfaces of fork pin holes formed in blade forks for turbine blades attached to the rotor of a steam turbine.

To facilitate the manufacturing and maintenance of a steam turbine used in a power generating plant, its rotational axis and turbine blades are manufactured separately and then assembled. Specifically, blade fork portions formed at the roots of the turbine blades are assembled to disc fork portions formed on a disc provided on the rotational axis of the steam turbine, and the turbine blades are fixed to the disc by inserting pins into fork pin holes formed in these fork portions (see FIG. 2 in Japanese Patent Laid-open No. 2001-12208). As the steam turbine rotates, stress is applied to the structural material of the turbine blade in the vicinity of the fork pin holes in the blade fork portion. Accordingly, cracks may be generated in the vicinity of the fork pin holes in the turbine blade.

Conventional inspection for cracks in the vicinity of the fork pin holes in the turbine blade is performed by removing the turbine blade from the disc and then applying magnetic particle testing (hereinafter referred to as MT). The MT is a method for detecting a leak of a magnetic flux from a defect in a test object when a magnetic field is applied to the test object. This MT is applied to the turbine blade, which is a test object, as described below. While a magnetic field is applied to the blade fork portion of the turbine blade, the surface of the blade fork portion is coated with magnetic metal particles on which a fluorescent material is applied, the fluorescent material being accumulated by the magnetic flux leaking from a defect. Ultraviolet rays are then irradiated to the blade fork portion. The magnetic metal particles accumulate in, for example, a defect in a fork pin hole. Since ultraviolet rays are irradiated, whether the magnetic metal particles accumulate can be determined by observing whether there is fluorescent light, and thus whether there is a defect can be determined. In inspection for defects on the basis of the MT, it is necessary not only to remove pins by which a disc fork portion of a disc and a blade fork portion of a turbine blade are joined but also to remove the turbine blade from the disc. When the turbine blade is inspected for defects on the basis of the MT, therefore, it takes much time. Upon the completion of the inspection, an additional task is needed to fit the turbine blade into the disc and combine them with pins.

Eddy current testing (ECT) is often used as a method of inspecting the surface of a test object for cracks. Particularly, the ECT is widely used to inspect the internal surfaces of tubular objects such as heat transfer tubes because an ECT probe can be moved quickly in the tube and thus advantages of functions suitable for high-speed ECT inspection can be fully taken. An example of ECT is described in Patent Laid-open No. Hei 8 (1996)-145954. In the ECT disclosed in Japanese Patent Laid-open No. Hei 8 (1996)-145954, a test probe including an ECT sensor is inserted into a tube to check whether the thickness of the tube is thinned and the interior is corroded.

SUMMARY OF THE INVENTION

However, ECT has not been used for inspection for cracks on the internal surfaces of fork pin holes in the steam turbine. As described later, the conventional ECT probe has not been sufficient to precisely detect the above crack generated on the internal surface of a fork pin hole.

An object of the present invention is to provide an eddy current testing apparatus and eddy current testing method that can further improve testing precision in eddy current testing.

A feature of the present invention for attaining the above object is that the diameter of a magnetic core used as an eddy current testing coil included in an eddy current testing sensor falls within the range of 0.1 mm to 0.5 mm. According to the present invention, in a structure in which blade fork portions formed at the roots of a plurality of turbine blades disposed along the periphery of the disc of a turbine rotor are joined with disc fork portion formed on the disc by use of pins, a crack which is generated on at least part of the internal surface of a hole formed through the disc fork portion and blade fork portion by pulling out the pin can be precisely detected. Particularly, in the present invention, it is possible to detect a minute crack that is generated near a juncture of two fork portions oppositely-disposed in adjacent blade fork portions, the juncture being formed on an internal surface of a groove formed by the facing surfaces of these fork portions, the internal surface being at least part of the internal surface of the hole.

To bring the diameter of the magnetic core within the range of 0.1 mm to 0.5 mm is a new fining obtained by the inventors, as described later.

Another feature of the present invention is to insert a probe having an eddy current testing sensor into the hole, which is formed through the disc fork portion and blade fork portion by pulling out the above pin while the blade fork portion is still inserted into the disc fork portion, and to perform eddy current testing for at least part of the internal surface of the hole. This feature can extremely shorten a time taken for the eddy current testing because it is not necessary to remove the turbine blade from the disc.

According to the present invention, testing precision in eddy current testing can be further improved.

BRIEF DESCRIPTION OF THE DRAWINGS

FIGS. 3A to 3C are a structural diagram showing a probe shown in FIG. 2.

DETAILED DESCRIPTION OF THE PREFERRED EMBODIMENT

Embodiments of the present invention will be described below.

Embodiment 1

An eddy current testing apparatus, which is a preferred embodiment of the present invention, inspects a blade fork portion formed at the root of a turbine blade provided on the rotor of a steam turbine and a disc fork portion formed on a disc. Specifically, the eddy current testing apparatus checks whether there is a crack on the internal surfaces of fork pin holes formed in a blade fork portion and a disc fork portion.

Figure 7:
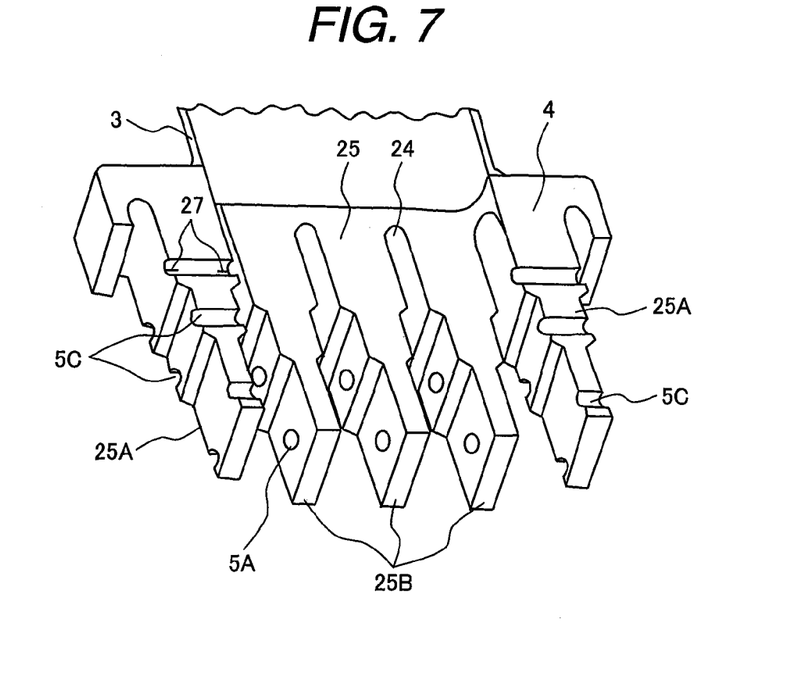
FIG. 7 is an enlarged perspective view showing the blade fork portion of a turbine blade under ECT inspection.
Figure 8:
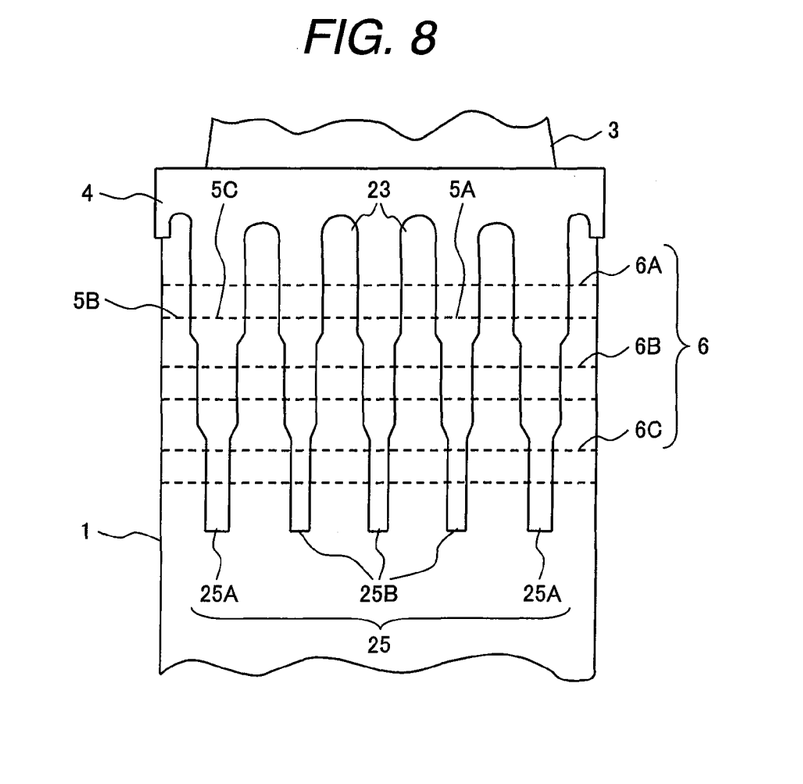
FIG. 8 is a structural diagram showing a combination portion of the blade fork portion and the disc fork portion.

Before explaining the eddy current testing apparatus in present embodiment, the structure of the rotor of the steam turbine will be schematically explained with reference to FIGS. 1, 7, and 8, the rotor having turbine blades and a disc being test objects. The rotor (not shown) in the steam turbine has turbine blades 3 at a plurality of stages, and is rotatably mounted in a turbine casing (not shown). The rotor forms the disc 1 on the rotary axis thereof. Many turbine blades 3 disposed along the periphery of the disc 1 are removably attached to the disc 1. A plurality of turbine blades 3 included in a turbine blade array in a single stage are mutually linked at their tops by a shroud 7.

How the disc 1 and turbine blades 3 are joined together will be specifically explained. Disc fork portions 2 are formed along the outer periphery of the disc 1, and blade fork portions 4 are formed at the roots of the turbine blades 3. The blade fork portion is a embedding portion of the blade 3. The shape of the disc fork portion 2 is such that a plurality of disc grooves 22 are formed in parallel in the axial direction of the rotor at fixed intervals. The disc fork portion 2 forms forks (fork projections) 23, each of which is between two adjacent disc grooves 22. For example, six forks 23 are formed in the disc fork portion 2 for each turbine blade 3. The blade fork portion 4 is stated by forming a plurality of fork grooves 24 at the root of the turbine blade 3 at fixed intervals. The blade fork portion 4 has forks (fork projections) 25, each of which is between two adjacent fork grooves 24. For example, five forks 25 constitute a blade fork portion 4. The number of forks 23 and the number of forks 25 vary with the turbine blades at different stages.

In each fork 23 of the disc 1, many fork pin holes (hereinafter simply referred to as pin holes) 5B are formed. The pin hole 5B is a round penetrated hole. Pin holes 5B are formed in each fork 23 for each of the turbine blades 3 disposed along the periphery of the disc 1 at fixed intervals. A plurality of pin holes 5B are also formed in a radial direction of the disc 1 at equal intervals. In present embodiment, three pin holes 5B are formed in a radial direction for each turbine blade 3. The pin holes 5B formed in the radial directions are concentric.

Of the forks 25 of the blade fork portion 4 disposed on single turbine blade 3, three forks located at the center are denoted forks 25B. These forks 25B each have a plurality of pin holes 5A, which are round penetrated holes. In present embodiment, each fork 25B has three pin holes 5A at equal intervals in the longitudinal direction of the fork 25B. The positions of the three pin holes 5A in the longitudinal direction match the positions of the three pin holes 5B formed in the forks 23 in the radial direction. Of the forks 25 of the blade fork portion 4, forks at both ends of the blade fork portion 4 are denoted forks 25A. These forks 25A each have a plurality of grooves 5C which have a shape resulting from cutting the pin hole 5A in half (the groove is referred to below as the half-round groove) and which are positioned at both ends facing in the peripheral direction of the disc 1. Three half-round grooves 5C are formed at the both ends each in the longitudinal direction of the fork 25A. The position of the half-round groove 5C at one end matches the position of the pin hole 5A formed in the fork 25B in the longitudinal direction of the fork 25. The position of the half-round groove 5C at the other end matches the position of the pin hole 5A formed in the fork 25B of another turbine blade 3 adjacent to the turbine blade 3 in the peripheral direction of the disc 1. The pin hole 5A, pin hole 5B, and half-round groove 5C have the same radius.

Each fork 25 of the turbine blade 3 is inserted into the disc grooves 22 respectively. In other words, each fork 23 of the disc 1 is inserted into a fork groove 24 of the turbine blade 3. In this state, a plurality of turbine blades 3 are lined up on the periphery of the disc 1 in the peripheral direction. The turbine blades 3 disposed like this are attached to the disc 1 by a plurality of fork pins 6. These fork pins 6 are inserted into the pin holes 5B formed in the forks 23, which are aligned in the axial direction of the rotor, the pin holes 5A formed in the forks 25B, and the half-round grooves 5C (see FIG. 8). Three fork pins 6 are inserted into each fork 25 of a single turbine blade 3. These fork pins 6 are an outer fork pin 6A, a middle fork pin 6B, and an inner fork pin 6C. The three fork pins 6 are disposed in a radial direction of the disc 1; the outer fork pin 6A is at the outermost position, the inner fork pin 6C is at the innermost position, and the middle fork pin 6B is at the middle position.

Figure 1:
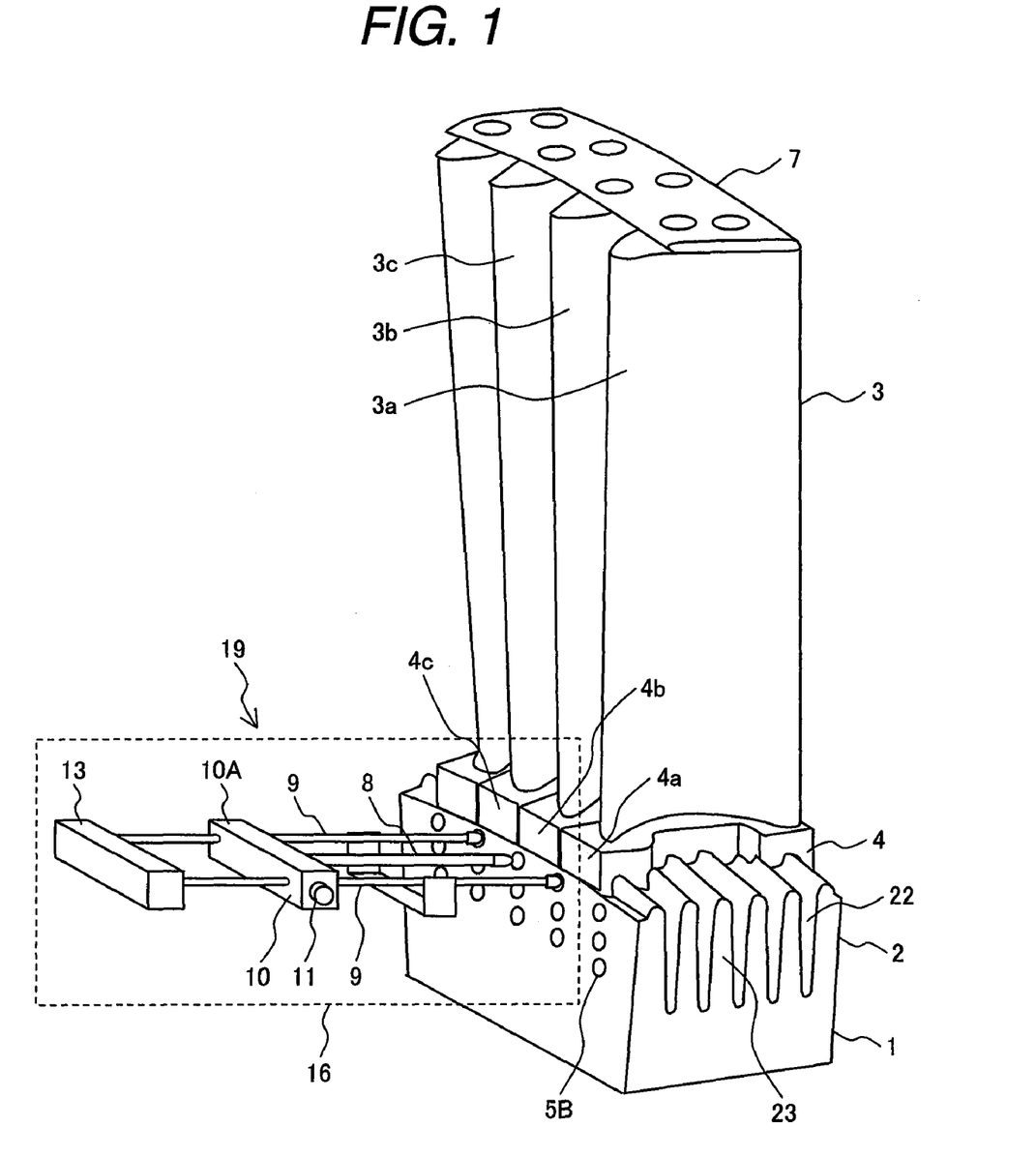
FIG. 1 is an explanatory drawing showing a state in which supporting rods of the eddy current testing apparatus shown in FIG. 2 are aligned to fork pin holes formed in a disc.
Figure 4:
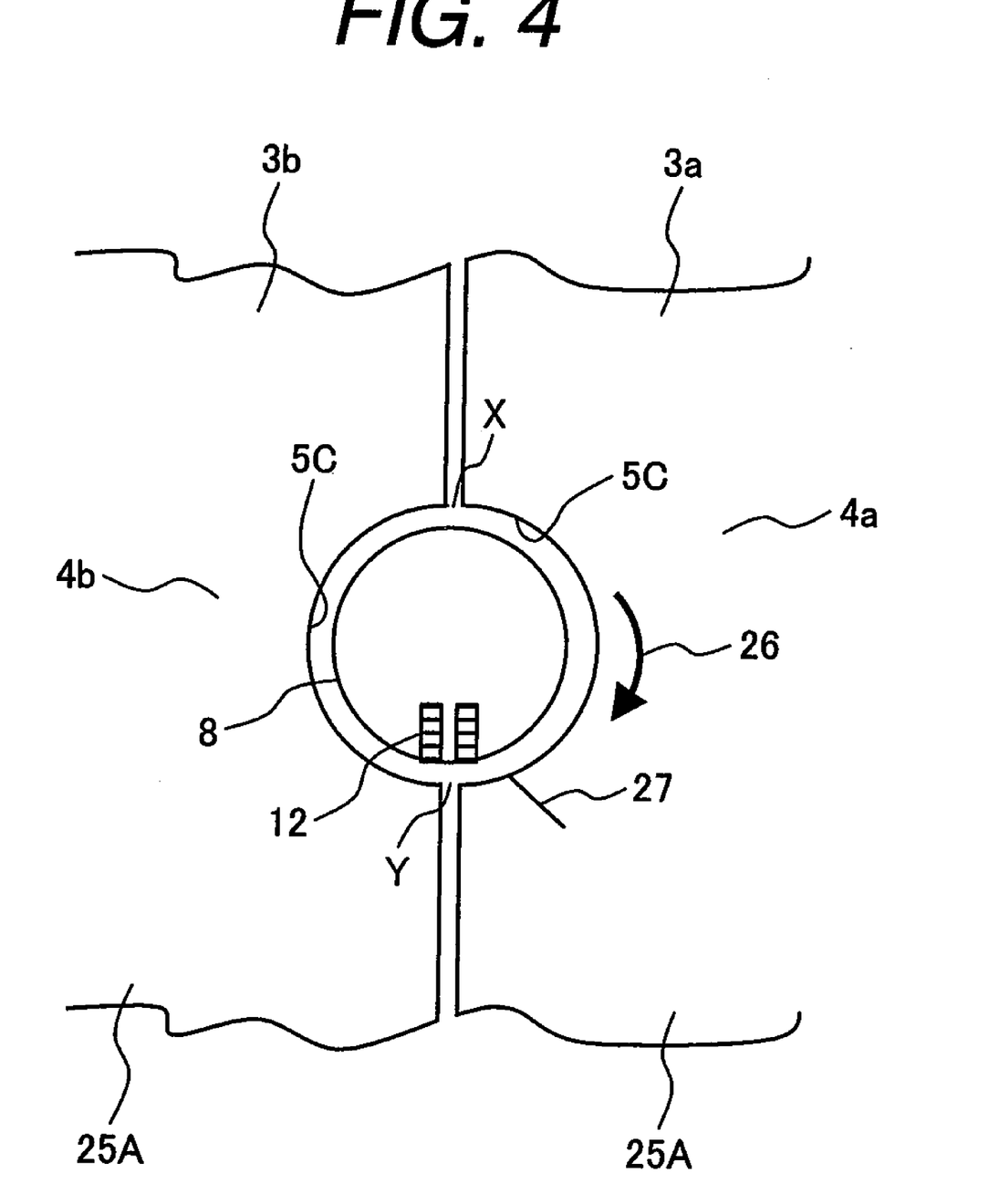
FIG. 4 is an explanatory drawing showing junctures between a fork of a blade fork portion 4a and a fork of a blade fork portion 4b, the blade fork portion 4a being adjacent to the blade fork portion 4b in the peripheral direction of the disc, and also the scanning by the probe.

Suppose that a plurality of turbine blades 3 are disposed on the disc 1 in the peripheral direction, as indicated by turbine blades 3a, 3b, and 3c shown in FIG. 1. One pin hole similar to the pin hole 5A is formed by half-round grooves 5C that are formed in the oppositely-disposed end surfaces of the forks 25A of the adjacent turbine blades 3a and 3b, the pin hole extending across these forks 25A (see FIG. 4). Junctures X and Y are formed between the oppositely-disposed forks 25A. The juncture Y is diametrically opposite to the juncture X.

Figure 2:
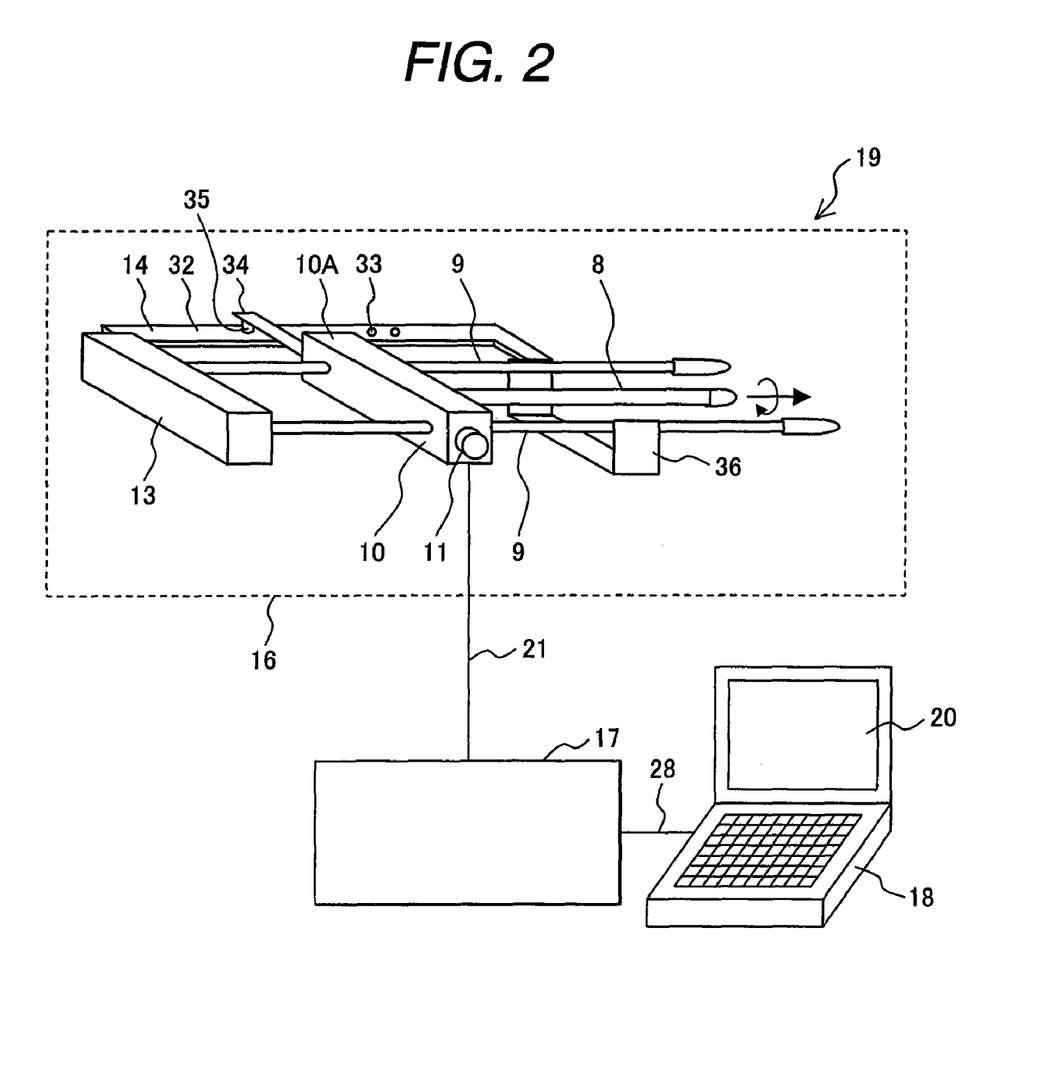
FIG. 2 is a structural diagram showing an eddy current testing apparatus according to a preferred embodiment of the present invention.

The eddy current testing apparatus in a preferred embodiment of the present invention will be described below in detail with reference to FIGS. 1 to 3. As shown in FIG. 2, the eddy current testing apparatus 19 in present embodiment has a sensor unit 16, an eddy current flaw detector 17, and a computer 18. The sensor unit 16 includes a probe 8, a pair of supporting rods 9, a flexible shaft portion 10, a supporting member 13, and a positioning device 14. The pair of supporting rods 9 are fixed to the supporting member 13. A linking member 36 links ends of the supporting rods 9. The pair of supporting rods 9 pass through a casing 10A of the flexible shaft portion 10. The flexible shaft portion 10 is movable along the supporting rods 9 in the axial direction of the supporting rods 9. The probe 8 is attached to the casing 10A and disposed between the pair of supporting rods 9. The ends of the probe 8 and supporting rods 9 are streamlined so that they can be inserted smoothly into pin holes. The outer diameters of the probe 8 and supporting rods 9 are the same as the inner diameters of the pin holes 5A and 5B. The end of the supporting rods 9 and the probe 8 may be replaceable according to the inner diameter of the pin holes formed in the disc 1 etc. The positioning device 14 is omitted in FIG. 1.

Figure 3A:
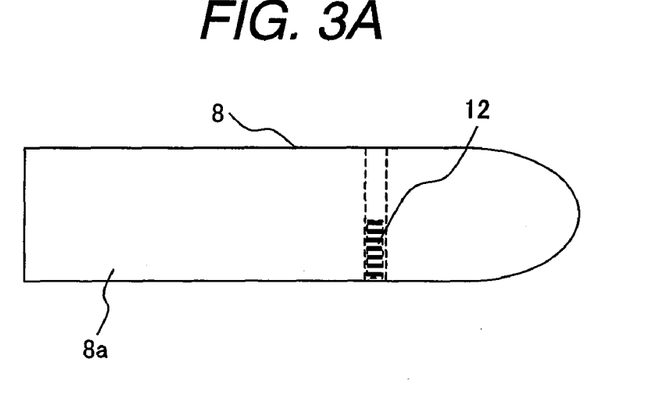
FIG. 3A is a side view of a probe having an ECT sensor.
Figure 3B:
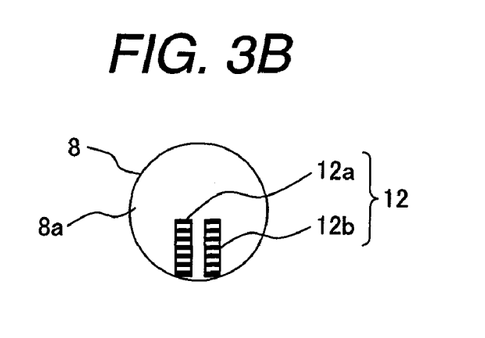
FIG. 3B is a cross sectional view of the probe at a position at which the ECT sensor is set.
Figure 3C:
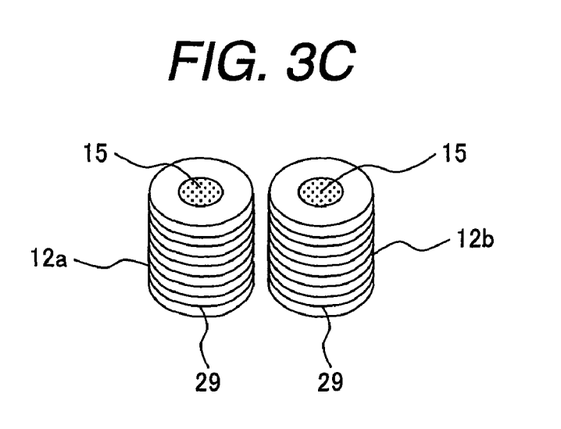
FIG. 3C is a perspective view of a pair of ECT coils included in the ECT sensor.

The probe 8 has an ECT sensor 12 is mounted in a main probe body 8a, as shown in FIGS. 3A and 3B. The ECT sensor 12 including ECT coils 12a and 12b is disposed at the end portion of the main probe body 8a. The ECT coils 12a and 12b are disposed side by side in the main probe body 8a, from the outer surface of the main probe body 8a toward the axial center of the main probe body 8a. A space is left between the ECT coils 12a and 12b in the peripheral direction of the main probe body 8a (see FIG. 3B). The ECT coils 12a and 12b are each structured by forming a coil 29 around a magnetic core 15 (see FIG. 3C). The magnetic core 15 is made of a magnetic material such as ferrite. Both the ECT coils 12a and 12b use a magnetic core 15 with diameter of 0.5 mm. The ECT sensor 12 is a self-induced ECT sensor based on a differential coil method. Both the ECT coils 12a and 12b use current to perform excitation and output detection signals. A feature of the self-induced ECT sensor based on the differential coil method in present embodiment is that when a metal member being the test object is made of a magnetic material and produces magnetic noise, the effect by the noise can be canceled with ease by detecting a difference between the signals from the two ECT coils 12a and 12b. When the effect by the noise is small, a cross correlation method, in which one of the two ECT coils 12a and 12b is used for excitation and the other is used for detection, or a self-inducing method, in which a single coil used, may also be applied.

In addition to the casing 10A, the flexible shaft portion 10 has a handle 11 rotatably attached to the casing 10A and a rotational force transmitting mechanism (not shown) disposed in the casing 10A. The rotational force transmitting mechanism has a rotational axis and a bevel gear and the like for transmitting the rotational force of the handle 11 to the probe 8. When the handle 11 is rotated, the probe 8 rotates. An angle meter (not shown) is attached at another end, which is in the casing 10A, of the main probe body 8a. The angle meter detects the rotational angle of the probe 8. Another handle and transmission mechanism (not shown) may be disposed in the supporting member 13 so that the pair of supporting rods 9 can be moved right and left with respect to the probe 8. When the other handle is rotated, the supporting rods are moved right or left and thereby the space between the supporting rods 9 can be adjusted according to the space between the pin holes 5B, as described later. To allow the pair of supporting rods 9 to move right and left, the penetrated holes formed in the casing 10A through which the supporting rods 9 pass need to be elongated to the right and left.

The positioning device 14 has a plate-like position setting member 32 and a stopper member 34. One end of the position setting member 32 is attached to the supporting member 13, and the other end is attached to one of the supporting rods 9. The position setting member 32 is disposed in parallel to the supporting rods 9 and outside the flexible shaft portion 10. When the flexible shaft 10 moves in the axial direction of the supporting rods 9, the movement is not restricted by the position setting member 32. A plurality of positioning holes 33 are formed in the position setting member 32 according to the positional relationship among the pin holes 5B, half-round grooves 5C, and pin holes 5A. The stopper member 34 is disposed on a side of the casing 10A and extends toward the position setting member 32. The stopper member 34 has a stopper portion 35 that can be inserted into and removed from the positioning hole 33. The stopper part 35 is structured in such a way that, for example, a metal ball movable in a cylindrical member in its axial direction is pressed downward by a coil spring. The metal ball does not come off the cylindrical member.

A power supply (not shown) for supplying excitation current and the coils 29 of the ECT coils 12a and 12b are connected with different wires. These wires are each provided with a switch (not shown) disposed in the casing 10A. A first switch is connected to the coil 29 of the ECT coil 12a, and a second switch is connected to the coil 29 of the ECT coil 12b.

A multi-conductor cable 21 is connected to the eddy current flaw detector 17 and extends up to the inside of the casing 10A of the flexible shaft portion 10. For example, a conductor included in the multi-conductor cable 21 is a signal line that is connected to the coil 29 of the ECT coil 12a and transmits a signal detected by the ECT coil 12a. Another conductor is a signal line that is connected to the coil 29 of the ECT coil 12b and transmits a signal detected by the ECT coil 12b. Another conductor transmits a switching command output from the eddy current flaw detector 17 to the first and second switches. Another conductor is connected to the above-mentioned angle meter. The eddy current flaw detector 17 is connected to the computer 18 through a cable 28. The computer 18 has a function for outputting control commands, such as an inspection start command and inspection termination command described later, and also has a signal processing function for processing ECT signals, which are output from the eddy current flaw detector 17 according to the signals detected by the ECT coils 12a and 12b. Accordingly, the computer 18 practically includes a controller for outputting control commands and a signal processor for processing its ECT signals.

Figure 5:
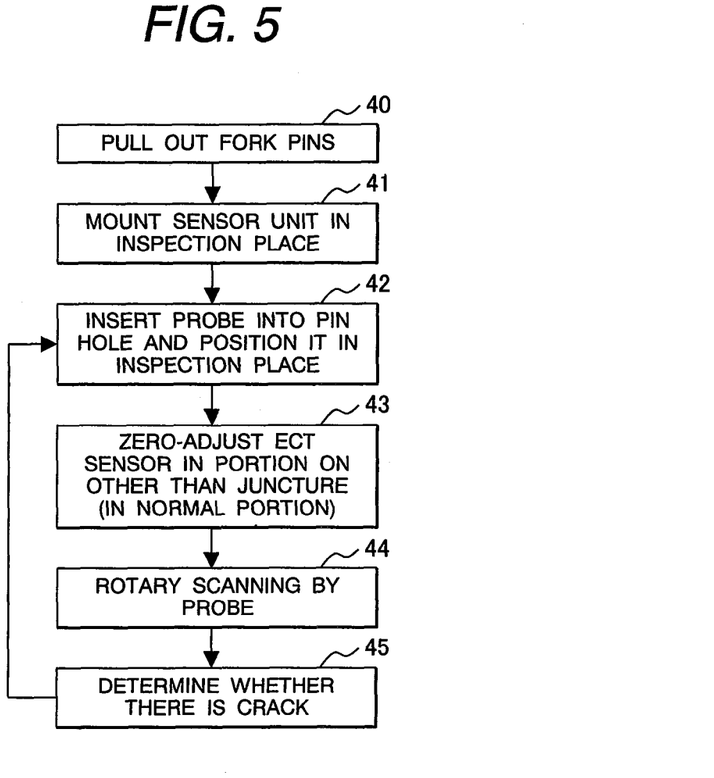
FIG. 5 is a flowchart showing a procedure executed in ECT inspection using the eddy current testing apparatus shown in FIG. 2.

As described above, the eddy current testing apparatus 19 is used to perform ECT inspection of the disc fork portion 2 of the rotor of the steam turbine and the blade fork portion 4. The ECT inspection will be described below in detail according to the flowchart, shown in FIG. 5, which comprises steps 40 to 45. First, the turbine casing is disassembled, and the rotor, on which a plurality of turbine blades 3 are disposed, is taken out from the turbine casing. The taken out rotor is rotatably placed on a pair of supporting bases mounted on the floor. Fork pins 6 are then pulled out of the disc 1 (step 40). In the process of removing the fork pins 6, the outer fork pins 6A, which are disposed at the outermost positions for a turbine blade array in a single stage, are all pulled out. Although all turbine blades 3 included in the turbine blade array face downward, they do not come off because they are joined with the disc 1 by the middle fork pins 6B and inner fork pins 6C.

The sensor unit 16 is mounted in an inspection place (step 41). The supporting member 13 of the sensor unit 16 is mounted on a supporting device (not shown) placed on the floor so as to be slidable in the axial direction of the supporting rods 9. The height of the supporting device can be adjusted according to the position of the pin hole under inspection. The targets that undergo ECT inspection are the internal surfaces of pin holes 5A and 5B and half-round grooves 5C into which an outer fork pin 6A has been inserted. Specifically, ECT inspection is performed for the internal surface of a pin hole 5B into which a single outer fork pin 6A has been inserted as well as the internal surfaces of a pin hole 5A and half-round grooves 5C on a single turbine blade 3. Upon the completion of the inspection, ECT inspection is performed for the internal surface of a pin hole 5B into which another outer fork pin 6A has been inserted, which is adjacent to the outer fork pin 6A in the peripheral direction of the disc 1 as well as the internal surfaces of a pin hole 5A and half-round grooves 5C on another turbine blade 3. For example, suppose that the internal surfaces of first pin holes under ECT inspection are the internal surface of the pin hole 5A, formed in the blade fork portion 4b of the turbine blade 3b, into which the outer fork pin hole 6A has been inserted, as well as the internal surfaces of the pin hole 5B and half-round grooves 5C on an extending line of the axial center of the pin hole 5A. The pin hole 5A, pin hole 5B, and half-round grooves 5C are collectively referred to below as pin holes under inspection. The probe 8 is inserted into the pin hole under inspection, as described later. The pair of supporting rods 9 are inserted into the pin holes 5A, into which the outer fork pin 6A has been inserted, formed in the blade fork portions 4a and 4c of the turbine blades 3a and 3c, each of which is adjacent to the turbine blade 3b in the peripheral direction, as well as into the pin holes 5B and half-round grooves 5C on extending lines of the axial center of these pin holes 5A. These pin holes 5A and 5B and the half-round grooves 5C, into which the supporting rods 9 are inserted, are collectively referred to below as supporting pin holes. In FIG. 1, the end portions of the pair of supporting rods 9 are aligned to two supporting holes, corresponding to the turbine blades 3a and 3c, into which the end portions of the supporting rods 9 will be inserted. When an operator manually slides the supporting member 13 with respect to the supporting device, the pair of supporting rods 9 are inserted into the corresponding supporting pin holes. When the pair of supporting rods 9 are inserted into the corresponding supporting pin holes, the sensor unit 16 is set at the inspection place. While the ECT inspection is in progress, the supporting rods 9 are held by the supporting member 13 mounted on the supporting device and the supporting pin holes. It is also possible to use an arrangement in which a motor is mounted in the supporting device so as to move the supporting member 13 toward the disc fork portion 2 by driving the motor.

Next, the probe 8 is inserted into the pin holes under inspection (step 42). Specifically, the operator manually moves the flexible shaft portion 10 toward the disc fork portion 2 by using the supporting rods 9 as a guide. Due to this movement, the end portion of the probe 8 is inserted into the pin holes, including the pin hole 5A formed in the blade fork portion 4 of the turbine blade 3b. The positioning device 14 positions the ECT sensor 12 attached to the probe 8 in the pin holes under inspection. Specifically, the positioning is performed by inserting the stopper portion 35 of the stopper member 34 into the positioning hole 33 formed in the position setting member 32 at a prescribed position. When the flexible shaft portion 10 is moved, the metal ball pushes the coil spring upward, so the stopper portion 35 easily comes off the positioning hole 33, making the flexible shaft portion 10 movable. The ECT sensor 12 is then positioned at a prescribed position, for example, an angular portion formed by two facing half-around grooves 5C formed in the forks 25A of the adjacent turbine blades 3b and 3a.

The ECT sensor 12 is zero-adjusted at a point on other than the junctures of forks of adjacent blade fork portions (step 43). A signal detected by the angle meter is input to the eddy current flaw detector 17 through the cable 21 and then input to the computer 18 through the cable 28. The computer 18, that is, the signal processing unit, outputs information about the rotational angle of the probe 8, which is detected by the angle meter, to a display unit 20. The operator determines whether the ECT sensor 12 faces a normal portion, that is, other than the junctures X and Y, with reference to the displayed information about the rotational angle. If the ECT sensor 12 faces one (X or Y) of the junctures, the operator rotates the handle 11 to turn the probe 8 so that the ECT sensor 12 faces a portion (preferably, a portion free from cracks) on the internal surfaces of the half-round grooves 5C between the junctures X and Y. In this state, the operator enters an inspection start signal from an input device (for example, a keyboard) connected to the controller. The controller (computer 18) outputs an inspection start command to the eddy current flaw detector 17 in response to the inspection start signal. Upon the input of the inspection start command, the eddy current flaw detector 17 outputs a start command to the first switch and second switch to close them. Excitation current is supplied from a power supply to the coils 29 of the ECT coils 12a and 12b. Eddy current is then generated on the surface of the half-round grove 5C, and currents inducted by the eddy current are generated in the coils 29. The currents generated in the coils 29 become signals detected by the ECT coils 12a and 12b and are input to the eddy current flaw detector 17 through the cable 21. The eddy current flaw detector 17 takes a difference between these detection signals by a circuit provided therein, and outputs the resulting ECT signal to the signal processing unit (computer 18). The ECT signal is output from the signal processing unit to the display unit 20 and displayed on the display unit 20. If the ECT signal is 0, it indicates that the ECT sensor 12 is zero-adjusted. If the ECT signal is not 0, the balance of a bridge circuit (or an equivalent circuit) provided in the eddy current flaw detector 17 is adjusted so that the ECT signal becomes 0. This completes the zero adjustment of the ECT sensor 12.

Upon the completion of the zero adjustment, the probe undergoes rotary scanning (step 44). Specifically, the operator operates the handle 11 to rotate the probe 8 one turn in the pin hole under inspection. In this rotary operation, the ECT sensor 12 rotates along the internal surfaces of the pair of half-round grooves 5C. ECT inspection is performed for the internal surfaces of the pair of half-round grooves 5C, which are included in the pin holes under inspection and face each other. Since exciting current is supplied to the ECT coils 12a and 12b, a detection signal output from the ECT coil 12a and another detection signal output from the ECT coil 12b are both input to the eddy current flaw detector 17, as described above. The eddy current flaw detector 17 outputs an ECT signal, which is a differential signal obtained according to both these detection signals. The ECT signal is input to the signal processing unit, in which the signal is processed. The signal processing unit creates image information that represents the relation between the amplitude of the ECT signal and the rotational angle by using, for example, the input ECT signal and the information about the rotational angle of the probe 8, which is input from the angle meter. This image information includes, for example, image information showing the relation between the X-direction component of the amplitude and the rotational angle and another image information showing the relation between the Y-direction component of the amplitude and the rotational angle. The signal processing unit outputs these image information to the display unit 20, and the display unit 20 displays these image information. When the above angle meter is not attached to the sensor unit 16, the signal processing unit creates image information that represents the relation between the amplitude of the ECT signal and time.

Figure 6A:
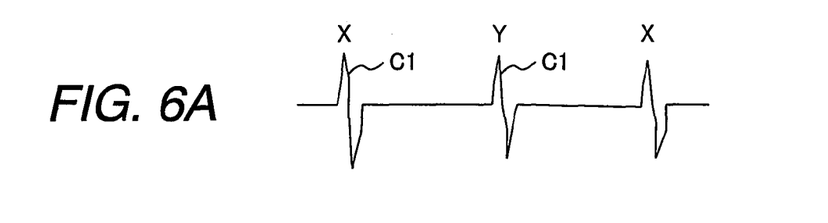
FIG. 6 is an explanatory drawing showing exemplary ECT signals output from the eddy current testing apparatus shown in FIG. 2.
Figure 6B:
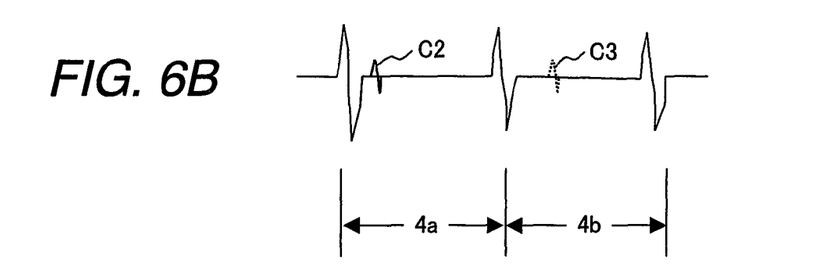

FIGS. 6A and 6B show exemplary ECT signals output from the eddy current flaw detector 17 to which signals detected by the ECT coils 12a and 12b are input in ECT inspection of the internal surfaces of the pair of half-round grooves 5C described above. Even in a normal state in which the internal surfaces of the pair of half-round grooves 5C are free from cracks, ECT pulses C1 with a large amplitude are generated at the junctures X and Y, in response to the shapes of the mating planes at the junctures X and Y (see FIG. 6A). At positions other than the junctures X and Y, the ECT signal is zero. When the internal surface of a half-round groove 5C has cracks 27, near the junctures, that extend the axial direction of the pin hole under inspection (see FIG. 7), the ECT signal output from the eddy current flaw detector 17 is, for example, as shown in FIG. 6B. In addition to the ECT pulses C1 generated at the X and Y junctures, the ECT signal includes ECT pulses with an amplitude larger than zero, the ECT pulses being generated at the positions at which the cracks are present. When the internal surface of a half-round groove 5C on the blade fork portion 4a includes a crack 27 near the juncture X, the ECT signal includes an ECT pulse C2 with an amplitude larger than zero at the position at which the crack 27 is present. When the internal surface of a half-round groove 5C on the blade fork portion 4b includes a crack 27 near the juncture Y, the ECT signal includes an ECT pulse C3 with an amplitude larger than zero. The cracks 27 generated on the internal surfaces of the half-round grooves 5C are small, so the amplitudes of the ECT pulses C2 and C3 are extremely smaller than the amplitude of the ECT pulse C1.

When a crack 27 is generated near the juncture X or Y, the conventional ECT sensor is affected by the ECT pulse C1 generated at the juncture, so the ECT pulse corresponding to an extremely small crack 27 cannot be separated from the ECT pulse generated at a juncture. Therefore, the conventional ECT sensor cannot detect a crack 27 generated near the juncture. The inventors examined various methods for detecting a crack 27 generated on the internal surface of a half-round groove 5C near its juncture, without being affected by the ECT pulse C1. The inventors then newly found through experiments that when the diameter of the magnetic core of the ECT sensor is 0.5 mm or less, the spatial resolution of the ECT sensor can be improved and thereby an ECT pulse generated on the internal surface of the half-round groove 5C near its juncture in response to the crack 27 can be separated from the ECT pulse at the juncture. However, when the diameter of the magnetic core is less than 0.1 mm, fabrication of the ECT coils become difficult. When the diameter of the magnetic core of the ECT sensor falls within the range of 0.1 mm to 0.5 mm, a crack 27 generated on the internal surface of a half-round groove 5C near its juncture can be detected.

Since the diameter of the magnetic core 15 is 0.5 mm in present embodiment, a crack 27 generated on the internal surface of a half-round groove 5C near its X or Y juncture can be detected.

Upon the completion of the ECT inspection for the above pair of half-round grooves 5C, the operator manually moves the flexible shaft portion 10 to move the probe 8 within the above pin holes under inspection, which corresponds to the blade fork portion 4b, so that the ECT sensor 12 is positioned at a position in other pin holes 5B and 5A in succession. The probe 8 is rotated at each position, and ECT inspection is performed at that position. Detection signals output from the ECT sensor 12 in the ECT inspection are input to the eddy current flaw detector 17 and output as ECT signals. The ECT signals are input to the signal processing unit and processed therein.

Whether there is a crack is determined (step 45). Specifically, the operator determines whether there is a crack on the internal surfaces of the half-round grooves 5C that have undergone ECT inspection, based on the information, which is displayed on the display unit 20, obtained in the ECT signal processing by the signal processing unit.

When the internal surface of any of the pin holes 5A and 5B and half-round grooves 5C, which are pin holes under inspection, does not have a crack, the flexible shaft portion 10 is manually moved to pull out the probe 8 from the pin holes under inspection. The supporting member 13 is also manually moved to pull out the pair of supporting rods 9 from the supporting pin holes. The next pin holes under inspection are the pin holes 5A and 5B and half-round grooves 5C into which an outer fork pin 6A, by which the turbine blade 3c adjacent to the turbine blade 3b is joined with the disc 1, has been inserted. The position of the sensor unit 16 is adjusted in the height direction so that the probe 8 faces the front of the next pin holes under inspection. Specifically, as described above, the supporting rods 9 are inserted into the supporting pin holes adjacent to this pin hole under inspection, and the probe 8 is then inserted into the pin holes under inspection. ECT inspection is performed for the internal surfaces of the pin holes and like under inspection. As described above, ECT inspection is performed for all pin holes under inspection into which all outer fork pins 6A have been inserted, the outer fork pins joining a turbine blade array in a single stage to the disc 1.

If a crack is found in a pin hole under inspection into which an outer fork pin 6A has been inserted, for example, in half-round grooves 5C as part of the pin holes under inspection including the outermost pin hole 5A in the blade fork portion 4b, the middle fork pin 6B for the turbine blade 3b is pulled out of the disc 1. Of the pin holes under inspection including the pin holes in which the middle fork pin 6B has been inserted, ECT inspection is performed, as described above, for the internal surfaces of the half-round grooves 5C inside the half-round groove 5C in which the crack has been found. If a crack 27 is also found in these half-round grooves 5C, the inner fork pin 6C disposed on the inner side is also pulled out. ECT inspection is performed for the internal surface of the half-round grooves 5C as part of the pin holes under inspection into which the middle inner fork pin 6C has been inserted. The middle fork pin 6B and inner fork pin 6C are inserted into the appropriate pin holes after the ECT inspection for their corresponding pin holes under inspection has been completed. Accordingly, if height adjustment by the supporting device is not possible, even when the rotor is rotated on a pair of supporting tables for alignment with the probe 8 before ECT inspection is performed for pin holes under inspection corresponding to another outer fork pin 6A, the inserted middle fork pin 6B and inner fork pin 6C prevent the turbine blade 3b from coming off.

After ECT inspection is completed for all pin holes under inspection corresponding to all the above outer fork pins 6A, new outer fork pins 6A, which are prepared separately, are inserted into appropriate pin holes formed in, for example, the disc 1, etc.

Of the pin holes 5A and 5B and half-round grooves 5C formed in each fork 25, which are included as pin holes under inspection, ECT inspection may be performed only for the internal surfaces of a pair of half-round grooves 5C that are located at the frontmost or backmost position in the direction of the insertion of the probe 8.

The present embodiment can improve detection accuracy for cracks because the ECT sensor 12 having the magnetic core 15 with a diameter of 0.5 mm is used. Particularly, it is possible to detect even a small crack 27 generated on internal surfaces of half-round grooves 5C near a juncture X or Y of forks 25A of adjacent blade fork portions 4a and 4b. In present embodiment, since the ECT coils 12a and 12b of the ECT sensor 12 are disposed so that their axial centers face the outer surface of the main probe body 8a, it is possible to easily detect a crack, on the internal surface of a pin hole 5A or 5B or a half-round groove 5C, that extends in the axial direction of the pin hole. Since the probe 8 is rotated, the entire inner surface of a pin hole or the like can be checked for a crack.

In present embodiment, the rotational angle of the probe 8 is also detected. When both the rotational angle and the ECT signal are considered, the operator can recognize which of the adjacent turbine blades 3a and 3b has a crack 27 on the internal surface of the half-round groove 5C formed on the blade fork portion 4, as illustrated in FIG. 6B. Furthermore, the operator can not only recognize the presence of the above crack 27 but also know its position in the peripheral direction by displaying rotational angle information and the ECT signals.

In ECT inspection, if the distance (referred to below as the liftoff) between the ECT sensor and the surface of the target under inspection changes, a signal detected and output also changes. In precise measurement of cracks, therefore, the change caused by a liftoff in the detection signal needs to be eliminated. To achieve this, the probe 8 must be firmly supported. However, the area around a disc fork portion 2, which undergoes ECT inspection in present embodiment, is narrow, so to find a way for supporting the probe 8 was a problem that is difficult to achieve. The inventors were insistent in studying solutions for eliminating liftoff factors when ECT inspection was performed for the internal surfaces of the pin holes under inspection in the disc fork portion 2 and blade fork portion 4. The inventors then arrived at a new idea that pin holes formed in the disc 1 etc. so as to accept fork pins 6 are used to hold the supporting member that supports the probe 8. A pair of supporting rods 9 were thus provided to the sensor unit 16 and inserted into two supporting pin holes formed in the disc 1 etc., near the pin hole under inspection (preferably, the supporting pin holes adjacent to the pin hole under inspection) so that the probe 8 is held by the pair of the supporting rods 9. Since, in present embodiment, the probe 8 is held by the supporting rods 9 that are inserted into supporting pin holes formed in the disc 1, etc. to accept fork pins 6, as described above, the probe 8 is firmly held with high precision. Accordingly, changes in liftoff can be substantially reduced and thereby liftoff-caused changes in detection signals output from the ECT coils 12a and 12b can be substantially reduced, improving crack detection precision. The supporting rods 9 function as a holding member and guide member for the probe 8 attached to the flexible shaft portion 10. It is also possible to support the probe 8 by inserting a single supporting rod into a supporting pin hole. However, when two supporting rods 9 are inserted into two supporting pin holes, as in this embodiment, the probe 8 is supported more firmly and thereby changes in liftoff can be made smaller.

In present embodiment, it suffices to remove only fork pins 6 that are present in an area to be subject to ECT inspection from the disc 1, etc., so the ECT inspection can be performed for the internal surface of a pin hole under inspection with the turbine blade 3 attached to the disc 1. This eliminates the need to remove the turbine blade 3 from the disc 1 when ECT inspection is performed for the fork portions, substantially shortening a time taken for ECT inspection to be performed for the disc fork 2 and blade fork 4. Furthermore, since ECT inspection is performed for the internal surface of a pin hole under inspection with the turbine blade 3 attached to the disc 1, ECT inspection can be performed for the internal surfaces of the pin holes formed in the disc fork 2 and blade fork 4 and the internal surfaces of the half-round grooves 5C formed in the blade fork 4 in succession with the probe 8 left inserted into the pin hole under inspection. This scheme also contributes to further shortening in ECT inspection time. One factor of shortening of the above ECT inspection time is an arrangement in which the supporting rods 9 are inserted into supporting pin holes.

In present embodiment, the outer fork pin 6A, disposed at the outermost position in a radial direction of the disc 1, is also pulled out, and ECT inspection is performed for the pin hole under inspection into which the outer fork pin 6A has been inserted. One turbine blade 3 is joined to the disc 1 by a middle pin 6B and an inner pin 6C, which are disposed in a radial direction of the disc 1. Due to this arrangement, even when all outer fork pins 6A disposed in a radial direction of the disc 1 are pulled out of a turbine blade array in a single stage during ECT inspection, the turbine blades 3 do not fall off the disc 1. In present embodiment, ECT inspection is first performed for the pin hole under inspection into which an outer fork pin 6A has been inserted. If a crack is found on the internal surface of the pin hole under inspection, ECT inspection is performed for the pin hole under inspection into which the middle fork pin 6B has been inserted, the middle fork pin 6B being positioned inside the outer fork pin 6A. In this embodiment, in which ECT inspection is performed as described above, the number of fork pins 6 pulled out of the disc 1 can be substantially reduced, so time taken in ECT inspection can be further shortened. The number of fork pins 6 to be attached to the disc 1 after the completion of the ECT inspection is also reduced, so working time taken to attach the fork pins 6 is also greatly shortened. While the steam turbine is operated, stress is generated in areas, in the fork, around the pin holes under inspection into which the fork pin 6 has been inserted. The stress in the area corresponding to the outer fork pin 6A is greater than the stress in the areas corresponding to the middle fork pin 6B and inner fork pin 6C. Accordingly, if there is no crack on the internal surface of the pin hole under inspection into which the outer fork pin 6A has been inserted, no cracks are generated on the internal surfaces of the pin holes under inspection into which the middle fork pins 6B and inner 6C have been inserted.

In present embodiment, of a plurality of fork pins 6 attached to the disc 1, all outer fork pins 6A attached at outermost positions are removed and ECT inspection is performed. It is also possible to remove all outer fork pins 6A, middle fork pins 6B, and inner fork pins 6C attached to the disc 1 within the range of, for example, a 120° area extending upward from the axial center of the disc 1 and then perform ECT inspection by using the eddy current testing apparatus 19 for all the pin holes under inspection into which these fork pins have been inserted. Upon the completion of the ECT inspection in this range, the removed fork pins 6 are attached to the disc 1, and the rotor is rotated so that another 120° area faces upward. All fork pins 6 are pulled out of the disc 1 in the other 120° area and ECT inspection is then performed. This ECT inspection is repeatedly performed for each 120° area.

In the above ECT inspection as well, the turbine blades 3 do not fall off the disc 1, eliminating the need to remove the turbine blades 3 from the disc 1. That is, when ECT inspection is performed by using the probe 8 for the internal surfaces of pin holes under inspection, the blade fork portions 4 can be left inserted into the disc fork portion 2. This ECT inspection takes a longer inspection time than in the embodiment described earlier, but takes a shorter inspection time than the conventional inspection in which the turbine blades 3 are removed from the disc 1 to check the blade fork portions for cracks.

What is claimed is:

1. An eddy current testing method for a turbine rotor comprising a disc, a plurality of turbine blades disposed along the periphery of said disc, and a plurality of pins for joining a blade fork portion formed on each of said plurality of turbine blades to a disc fork portion formed on said disc, the method comprising the steps of:

inserting a probe having an eddy current testing sensor into a hole formed through said disc fork portion and said blade fork portion by pulling out one of the plurality of pins in a state that said blade fork portion is still inserted into said disc fork portion; and performing eddy current testing for at least part of an internal surface of said hole by using said probe.

2. The eddy current testing method according to claim 1, wherein said one of said portion of said plurality of pins to be pulled out is disposed at an outermost position of said plurality of pins disposed in a radial direction of said disc and joining said blade fork portion to said disc fork portion.

3. The eddy current testing method according to claim 1, wherein said probe having said eddy current sensor which includes a magnetic core with a diameter within the range of 0.1 mm to 0.5 mm.

4. An eddy current testing method for a turbine rotor comprising a disc, a plurality of turbine blades disposed along the periphery of said disc, and a plurality of pins for joining a blade fork portion formed on each of said plurality of turbine blades to a disc fork portion formed on said disc, the method comprising the steps of:

pulling a portion of said plurality of pins out of said disc fork portion and said blade fork portion;

inserting a probe having an eddy current testing sensor into one of a plurality of holes formed through said disc fork portion and said blade fork portion by pulling out said portion of said plurality of pins in a state that said blade fork portion is still inserted into said disc fork portion; and performing eddy current testing for at least part of an internal surface of said one of a plurality of holes by using said probe.

5. An eddy current testing method for a turbine rotor comprising a disc, a plurality of turbine blades disposed along the periphery of said disc, and a plurality of pins for joining a plurality of blade fork portions formed correspondingly on each of said plurality of turbine blades to a disc fork portion formed on said disc, each of said turbine blades being joined to the disc by said plurality of pins disposed in a radial direction of said disc, the method comprising the steps of:

pulling a portion of said plurality of pins, disposed at an outermost position of said plurality of pins disposed in a radial direction for each of said turbine blades, out of said disc fork portion and said corresponding plurality of blade fork portions;

inserting a probe having an eddy current testing sensor into each of a plurality of holes, which are formed through said disc fork portion and said corresponding plurality of blade fork portions by pulling said portion of said plurality of pins disposed at said outermost position in succession in a state that said corresponding plurality of blade fork portions are still inserted into said disc fork portion; and performing eddy current testing for at least part of an internal surface of each of said plurality of holes by using said probe.

6. The eddy current testing method according to claim 5, further comprising the steps of:

pulling out another one of said plurality of pins disposed inside said portions of said plurality of pins disposed at said outermost position and joining one of said blade fork portion to said disc fork portion, when there is a crack on at least a part of the internal surface of one of said plurality of holes formed through one of said blade fork portions; and inserting said probe into another hole formed through said disc fork portion and said one of said blade fork portions by pulling said another one of said plurality of pins.

* * * * *